United States Patent [19]

Rodier

[11] Patent Number: 5,401,268

[45] Date of Patent: Mar. 28, 1995

[54] FASTENING DEVICE FOR SANITARY PRODUCTS

[75] Inventor: Hubert Rodier, Montpellier, France

[73] Assignee: Prest'Hyg S.A., France

[21] Appl. No.: 211,745

[22] PCT Filed: Jul. 1, 1993

[86] PCT No.: PCT/FR93/00671

§ 371 Date: Apr. 14, 1994

§ 102(e) Date: Apr. 14, 1994

[87] PCT Pub. No.: WO94/04110

PCT Pub. Date: Mar. 3, 1994

[30] Foreign Application Priority Data

Aug. 14, 1992 [FR] France .................... 92 10052
Jan. 27, 1993 [FR] France .................... 93 00829

[51] Int. Cl.$^6$ .............................................. H61F 13/20
[52] U.S. Cl. ................................. 604/385.1; 604/383
[58] Field of Search ................. 604/385.1, 383, 387, 604/386, 389, 390

[56] References Cited

U.S. PATENT DOCUMENTS

| 4,500,316 | 2/1985 | Damico | 604/385.1 |
| 4,781,712 | 11/1988 | Barabino et al. | 604/385.1 |
| 4,950,264 | 8/1990 | Osborn, III | 604/385.1 |
| 5,201,727 | 4/1993 | Nakanishi et al. | 604/389 |

FOREIGN PATENT DOCUMENTS 284589 11/1990 Germany ............ 604/385.1

Primary Examiner—Jerome L. Kruter
Attorney, Agent, or Firm—Bierman and Muserlian

[57] ABSTRACT

A feminine hygiene sanitary towel with fastening tabs arranged asymmetrically along the longitudinal edge of a sanitary towel, the adherent part of which is the inner part for the user of this towel and which is an integral part of the towel and a production process for sanitary products fitted with these lateral flaps, which consists of confining the absorbent pad made of cellulose pulp or of a sanitary towel composite, between a film of polyethylene and a layer of non-woven fabric or a film of microperforated polyethylene which is impermeable to liquids towards the outside, of sealing the two layers by sizing or heat-sealing, of cutting, along the strip, the material formed previously, constituted by the pad and the two protective layers of impermeable film to a wavy ribbon in the form of a garland, placing this garland on a single-sided siliconized paper, the inner side of which has been coated beforehand in a continuous or discontinuous manner with a glue, and placing a second single-sided siliconized paper, the inner side of which has been coated beforehand with one or more blocks of glue, on the lateral flaps which have been folded over the inner surface.

1 Claim, 6 Drawing Sheets

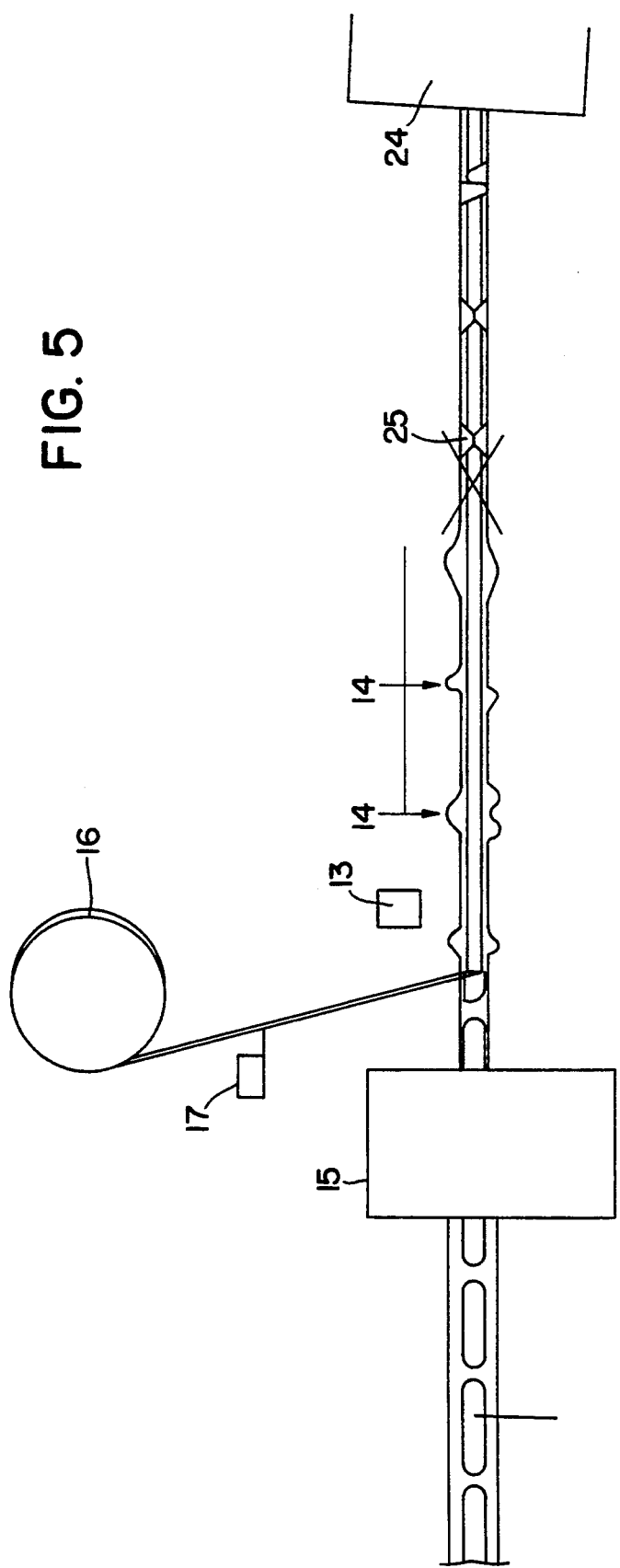

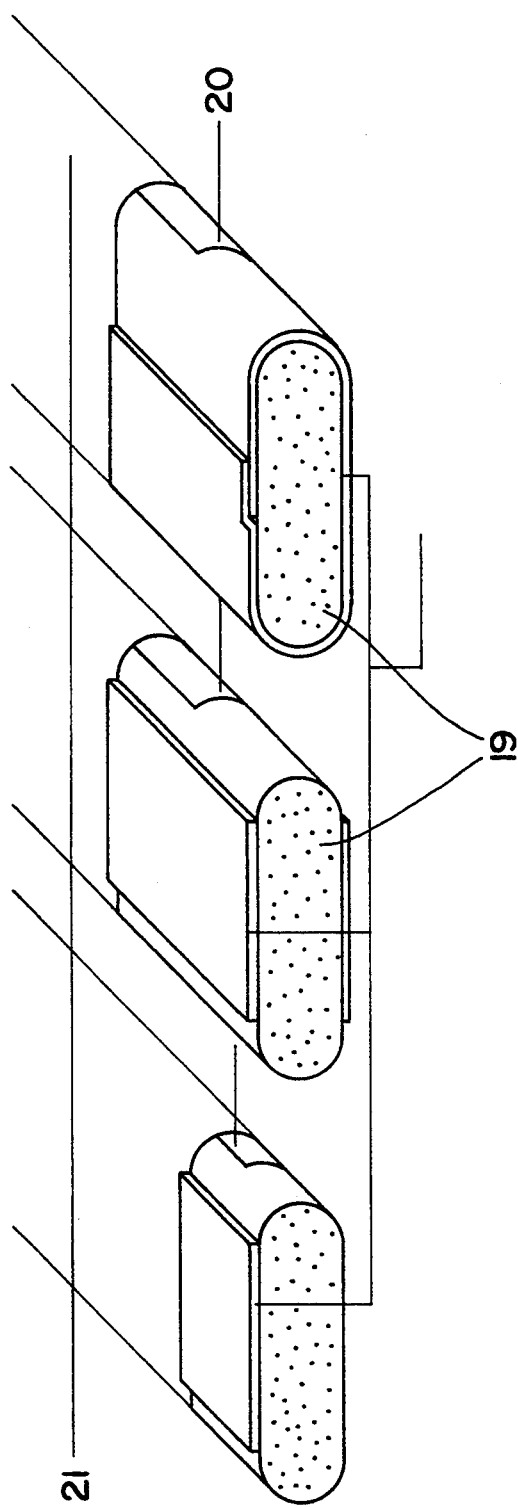

FASTENING DEVICE FOR SANITARY PRODUCTS

BACKGROUND OF THE INVENTION

The present invention relates to the field of hygiene and more particularly to that of feminine hygiene.

A particular subject of the invention is moveable fastening tabs or wings placed on the outer surface of sanitary towels and arranged asymmetrically along the longitudinal edge of the sanitary towel.

In fact, it is known from European Patent Application 0,134,086 (PROCTER & GAMBLE), from European Patent Application 0,267,059 (BEGHIN-SAY) or also from International Patent Application WO 89/02729 that it is possible to provide, during the cutting of the outer lining of sanitary towels, lateral flaps of semi-circular or quadratic shape designed so as to form after use, by folding around the sanitary towel, itself folded, a disposable sealed package. According to European Patent Application 0,267,059, the presence of lateral wings or flaps in the area of the biconcave zone of the inner surface of the sanitary towel provides, in addition, improved lateral impermeability as well as excellent comfort.

In this Patent Application, the lateral wings or flaps contain, in addition, one or more layers, joined together, improving the lateral impermeability. The fixing of these wings is provided by the cutting method because they are an integral part of the towel.

It was however desirable to find a fastening device which provides a surface for fixing on the under-garment which is larger than that presented by the current devices with lateral flaps and at the same time, which guarantees surface evenness and therefore lateral impermeability without having recourse to complex industrial methods.

The example with asymmetrical wings defined in French Patent Application 92.10052 in the name of the Applicant already provides an initial solution.

The purpose of the device according to the invention is to obtain this desired new result.

SUMMARY OF THE INVENTION

It is characterized in that the lateral flaps are incorporated in the gauze and in the impermeable part.

The lateral flaps according to the invention have a triangular surface projecting over the median axis of the outer part of the sanitary towel which may contain, on its base, a semi-circular indentation.

The two lateral flaps are arranged head-to-tail on the towel, so as to provide an adhesion surface which is as large as possible.

Before use, the flaps are lateral and are folded under the adhesive surface or surfaces of the single-sided siliconized paper, placed on the inner surface, which permits the subsequent transfer of the adhesive surfaces onto the lateral flaps at the time of use.

The invention also includes a process for the production of sanitary products provided with these lateral flaps which consists of confining the absorbent pad made of cellulose pulp or of a sanitary towel composite, between a film of polyethylene and a layer of non-woven fabric or a film of micro-perforated polyethylene which is impermeable, towards the outside, to liquids, of sealing the two layers by joining or sizing, of cutting, along the strip, the material formed previously, constituted by the pad and the two protective layers of impermeable film, thus forming a wavy ribbon in the form of a garland, of placing this garland on a single-sided siliconized paper the inner side of which has been coated beforehand in a continuous or discontinuous manner with a glue. A second single-sided siliconized paper, the inner side of which has been coated beforehand with one or more blocks of glue, is placed on the lateral flaps which have been folded beforehand over the inner surface.

According to one particular example of the invention, the sealing of the polyethylene film is carried out by heat-sealing or by sizing.

In the latter case, an elastic cylindrical membrane maintained under pressure ensures contact between the two layers of film with a view to sealing.

The cutting out of the lateral flaps is carried out in a synchronous fashion and at the same time as the positioning of the absorbent pads.

The positioning of the single-sided siliconized paper is carried out after the cutting of the ribbon in the form of a garland. Nevertheless, in a variant of the process of the embodiment according to the invention, the positioning can also be carried out before the cutting of the garland.

BRIEF DESCRIPTION OF THE DRAWINGS

FIGS. 4 and 5 illustrate schematically the machines for producing the sanitary towel of FIG. 1.

FIG. 6 is a cross-sectional view of the sanitary towel showing the fixing of straps onto the permeable film.

Figure 1:
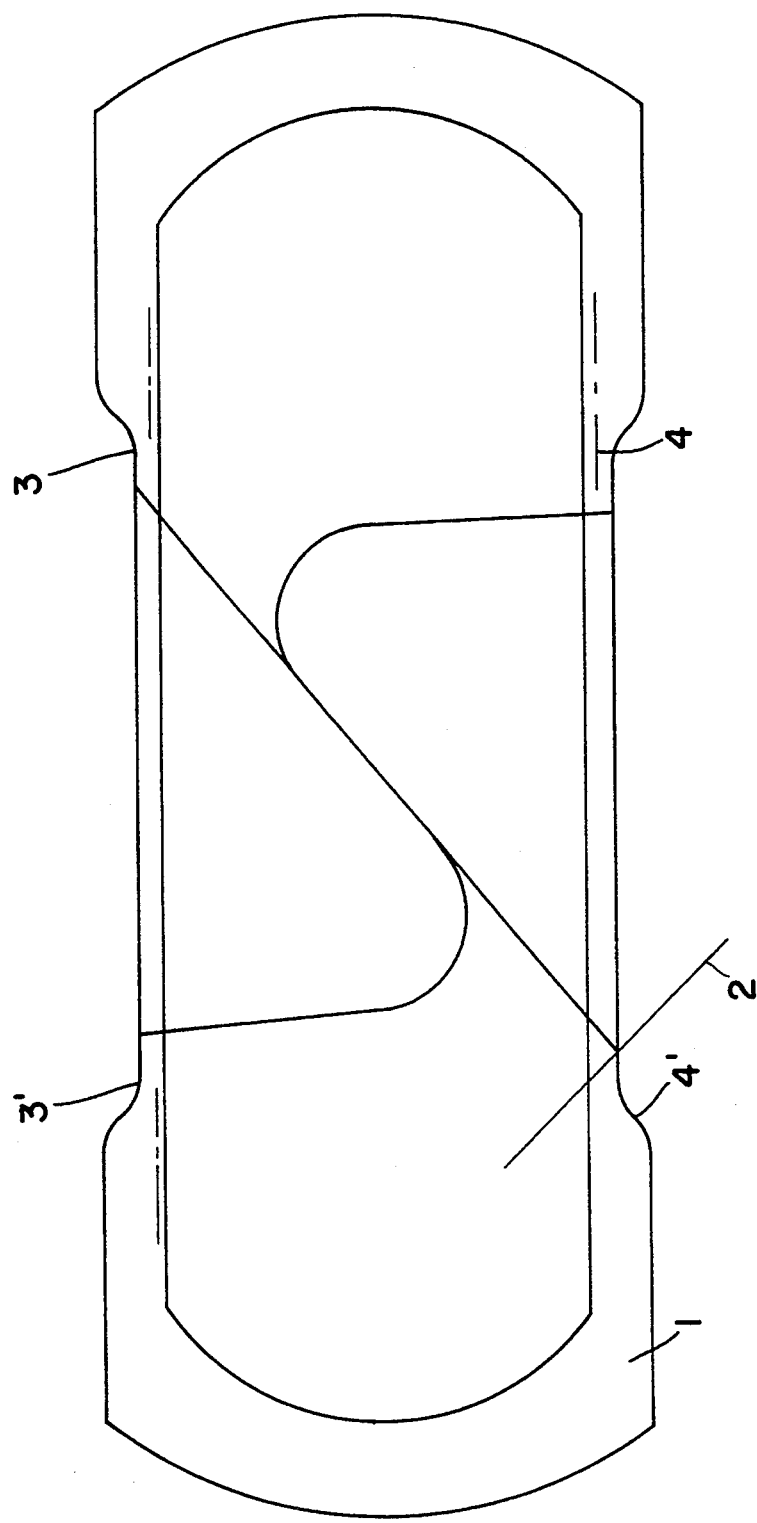
FIG. 1 is a plan view of a sanitary towel of the invention with the lateral flaps in the initial stage.

According to a particular method for implementing the invention, shown in FIG. 1, a sanitary towel is shown seen from the front, comprising two lateral flaps arranged asymmetrically and folded over the inner surface of the sanitary towel.

The following elements are shown: the perforated outer gauze (1) of the sanitary towel, the central adhesive part (2) of the sanitary towel, the two sets of indentations (3) and (3') on the one hand and (4) and (4') on the other hand, positioned on the surface where the lateral flaps are inserted on the outer gauze.

Figure 2:
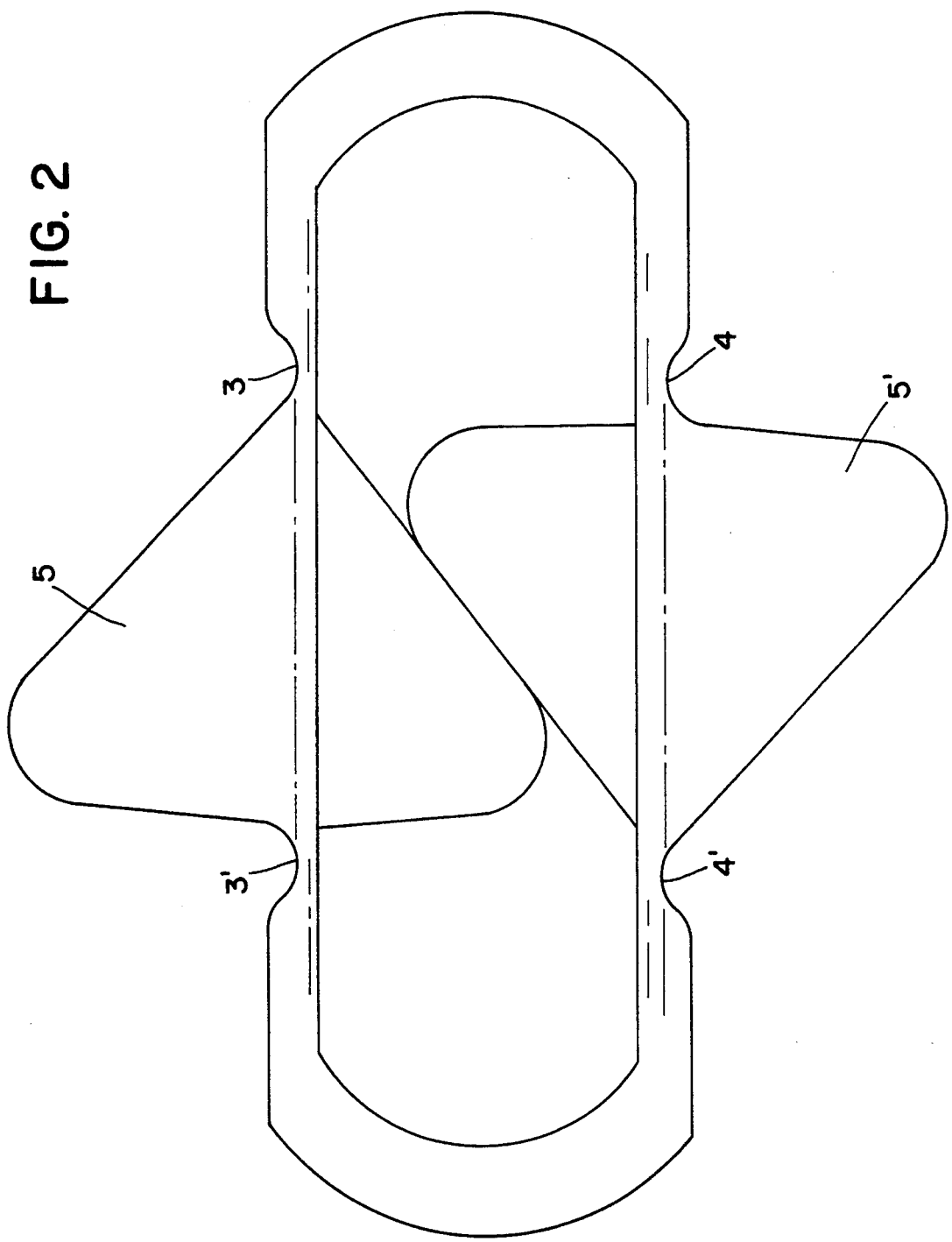
FIG. 2 is a plan view of the sanitary towel of FIG. 1 with the lateral flaps open.

FIG. 2 shows the two lateral flaps opened out with a view to use each shown with an adhesive surface (5) and (5'). According to various methods for implementing the invention, these adhesive surfaces can be either larger in order to occupy a part of all of the lateral flap, or also be presented in the form of several glued and offset surfaces. FIG. 2 also shows the indentations (3) and (3') on the one hand and (4) and (4') on the other hand, highlighting the use of these areas for ensuring the complete opening out of the flaps.

Figure 3:
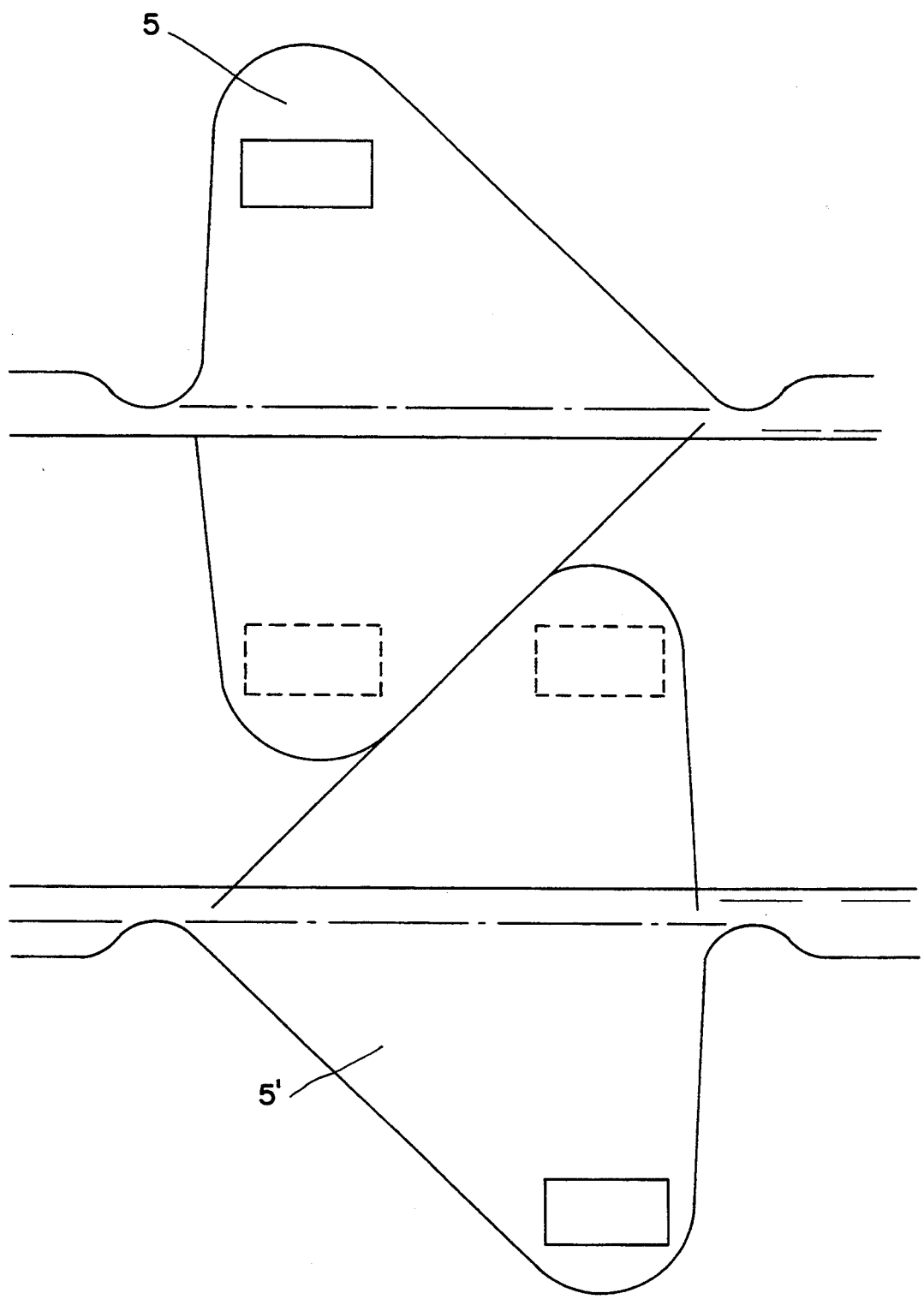
FIG. 3 is an enlarged view of the overlapping flaps when folded down.

FIG. 3 shows an enlarged view of the overlapping of the two lateral flaps when they are folded down, or their asymmetrical position relative to the axis of symmetry of the sanitary towel when they are opened out.

The triangle created by the lateral edge of the flap and the edge of the polyethylene gauze and of the upper non-woven fabric or gauze, has an apex angle of about 50°, whilst the apex angle of the same triangle when the lateral flap is folded over the sanitary towel is about 80°.

The asymmetry of the two lateral flaps-permits the complete folding-over of these after processing along one of the sides of the triangle thus created, so occupying the minimum of space in the packaging.

Other embodiment examples are also possible without exceeding the scope of the present invention.

Figure 4:
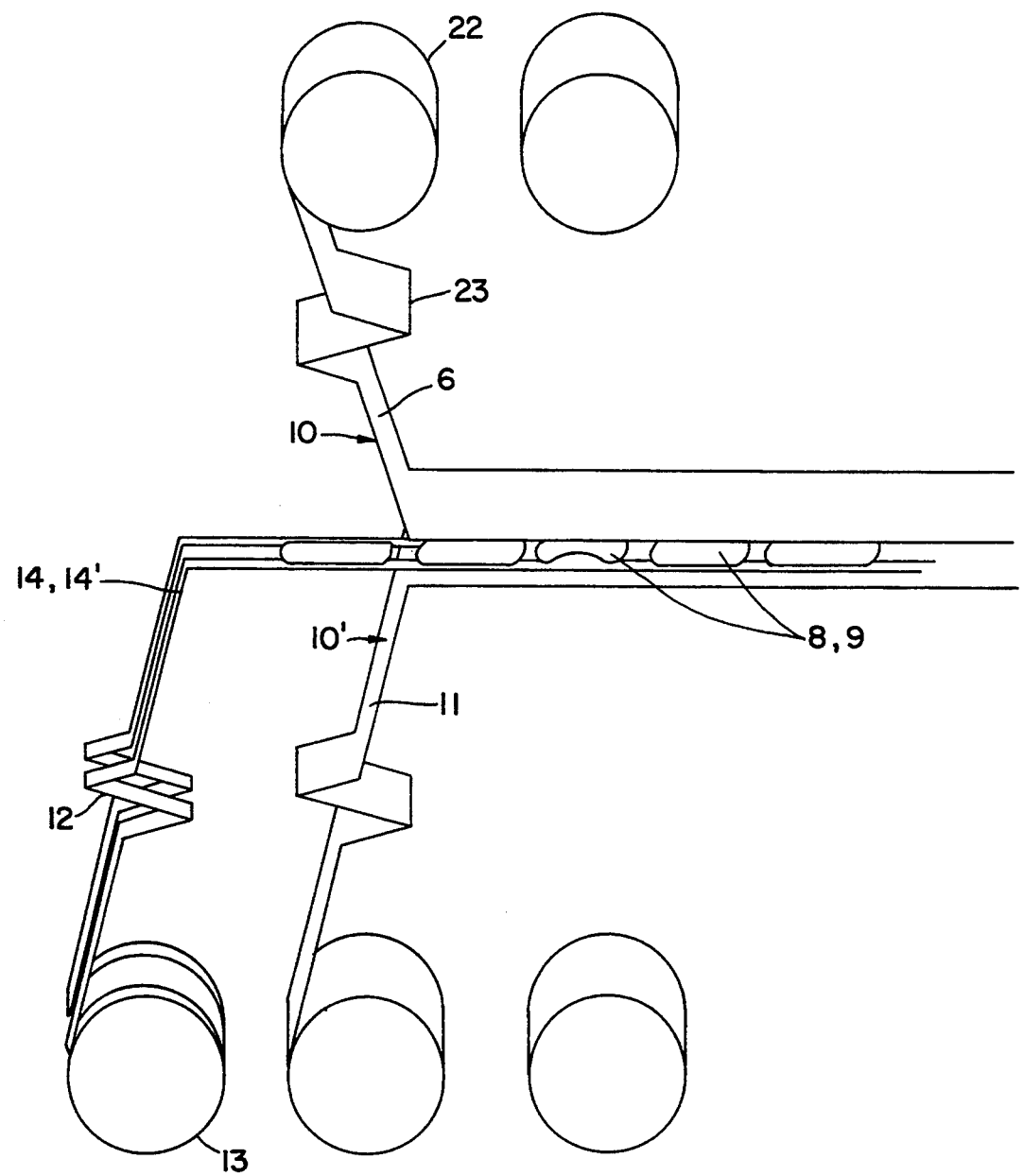

The invention also consists of the production of a kit adaptable to all existing manufacturing machines, using traditional manufacturing processes schematized in FIGS. 4, 5 and 6.

On these machines, the process for producing the absorbent mass is not modified relative to the technology but the first difference resides in the fact that a woven or non-woven fabric, or any other material permitting an increase in the diffusion of the flow, is added. The kit therefore comprises, firstly, unwinding and folding machines enabling the absorbent mass to be covered or encased by this additional material for improving diffusion.

The second modification of the machines consists of the installation of a calendering stand enabling leakages through the sides of the product to be limited. The type of calendering is very important. The absorbent pad or mass (8) is therefore produced with its diffusing material (9) and can allow the manufacturing process to proceed, which is carried out continuously. Once it is finished, the pad is placed on the polyethylene (6) or on the non-woven fabric (or a microperforated film) which has been glued beforehand for this operation. The kit therefore contains a gluing system (10) as well as a stand (22) for unwinding the material evenly in order to have the desired tension and a bar feeder system (23) permitting the film to be regulated and stretched. The same station is designed to cover the pad and "sandwich" it between the two layers of film (11). The addition of two impermeable strips (14) and (14') on the sides of the pad can be adapted according to the manufacturing requirements and therefore necessitates an additional unwinder (13) also fitted with a bar feeder (12) and a tension regulating system which is not shown. The lateral strips are then cut at a cutting station (15).

The whole of the cloth thus produced can then be subjected to compression treatment (24) in order to obtain good cohesion.

FIG. 6 shows the fixing of the two impermeable strips (14) and (14') on which the permeable film is fitted.

Several variants are proposed with the kit:
1. level difference compression, the cloth which is worked flat and continuously, passes between several compression cylinders.
2. compression by a system of flexible and inflatable cylinders, which allow the shape of the product to be compressed and moulded.
3. cutting in the form of a garland but only cutting the edges of the product.
4. cutting around the entire circumference of the product.
5. manufacture of the product on a machine with its outer face upwards.
6. manufacture of the product on a machine with its outer face downwards.

Once a good cohesion of the cloth is obtained, one passes to the following stage: lateral cutting of the product in order to obtain the fastening tabs.

The assembly kit therefore comprises, in addition, a cutting station (15) for continuous or intermittent cutting, which allows the lateral fastening tabs to be produced (the kit allows 1 to 10 tabs to be produced according to the final use of the product). These tabs can be asymmetric or symmetric (14) and (14').

The scraps are drawn off and collected in sacks.

One or more single-sided siliconized papers (16) coated with glue on one side (17) are placed on the cloth.

The kit therefore also comprises a system for positioning and unrolling the silicon paper (16) and (16') as well as the gluing material (17) and (17'). The problem which is then posed consists precisely of folding down the tabs and applying the blocks of glue to the tabs by means of the siliconized paper. This is why the kit according to the invention also contains a folding stand (25), a compression station (24), as well as a cutting station for the siliconized paper (26). Once the product is finished, all that remains is to cut it to its final length, fold it and pack it individually or leave it flat for use.

The towel therefore has a siliconized paper on the outer surface as well as on the tabs which are on the inner surface. At the time of use, firstly the silicon paper is removed from the outer surface in order to apply it to the bottom of the panties and, secondly, only the silicon paper which is on the fastening tabs is removed.

The sanitary towel according to the invention is therefore usable with only 4 handling operations whereas for an example with 2 symmetrical fastening tabs the number of handling operations is significantly higher.

A subject of the invention is:
What is claimed is:
1. Lateral fastening tabs placed on the outer surface of sanitary towels and arranged asymmetrically along the longitudinal edge of the protection device characterized in that they are formed of two triangular pieces (2) projecting over the median axis of the outer sheet (1) of the external protection device optionally containing semi-circular indentations (3)(3')(4)(4') on the base and a rounded cutout at the top and at the base of the triangular piece and in that the triangular pieces already folded over the inner surface are covered, on the inner side, by the adhesive surface or surfaces of the single-sided siliconized paper.

* * * * *